US006767741B1

(12) United States Patent
Epstein et al.

(10) Patent No.: US 6,767,741 B1
(45) Date of Patent: Jul. 27, 2004

(54) METAL BINDING COMPOUNDS AND THEIR USE IN CELL CULTURE MEDIUM COMPOSITIONS

(75) Inventors: David A. Epstein, East Amherst, NY (US); Paul J. Battista, Eggertsville, NY (US); Dale F. Gruber, Grand Island, NY (US); David A. Judd, Williamsville, NY (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/650,339

(22) Filed: Aug. 28, 2000

Related U.S. Application Data

(60) Provisional application No. 60/151,055, filed on Aug. 27, 1999.

(51) Int. Cl.$^7$ .................................................. C12N 5/00
(52) U.S. Cl. ....................................... 435/404; 435/405
(58) Field of Search .............................. 435/325, 329, 435/384, 404, 405

(56) References Cited

U.S. PATENT DOCUMENTS

| | | | |
|---|---|---|---|
| 4,205,126 A | 5/1980 | Cartaya ........................... 435/2 |
| RE30,985 E | 6/1982 | Cartaya ......................... 435/240 |
| 4,533,637 A | 8/1985 | Yamane et al. ............... 435/240 |
| 4,550,101 A | 10/1985 | Hider et al. .................. 514/188 |
| 4,575,502 A | 3/1986 | Hider et al. .................. 514/184 |
| 4,650,793 A | 3/1987 | Hider et al. .................. 514/188 |
| 4,665,064 A | 5/1987 | Hider et al. .................. 514/184 |
| 4,666,927 A | 5/1987 | Hider et al. .................. 514/350 |
| 4,767,704 A | 8/1988 | Cleveland et al. ............. 435/68 |
| 4,834,983 A | 5/1989 | Hider et al. .................. 424/463 |
| 4,861,767 A | 8/1989 | Hider et al. .................. 514/184 |
| 4,879,222 A | 11/1989 | Alderman et al. ............. 435/68 |
| 4,908,371 A | 3/1990 | Moerker et al. ............... 514/318 |
| 4,912,118 A | 3/1990 | Hider et al. .................. 514/302 |
| 5,045,454 A | 9/1991 | Bertheussen ................. 435/29 |
| 5,045,468 A | 9/1991 | Darfler ..................... 435/240.31 |
| 5,057,302 A | 10/1991 | Johnson et al. ................ 424/1.1 |
| 5,061,815 A | 10/1991 | Leu .............................. 556/118 |
| 5,118,513 A | 6/1992 | Mehansho et al. .............. 426/2 |
| 5,135,866 A | 8/1992 | Heifetz et al. ........... 435/240.31 |
| 5,177,068 A | 1/1993 | Callingham et al. .......... 514/184 |
| 5,202,451 A | 4/1993 | Fritzberg et al. ............. 556/419 |
| RE34,313 E | 7/1993 | Hider et al. .................. 514/188 |
| 5,227,474 A | 7/1993 | Johnson et al. ............... 534/558 |
| 5,232,848 A | 8/1993 | Wolfe et al. ............ 435/240.31 |
| 5,256,676 A | 10/1993 | Hider et al. .................. 514/348 |
| 5,278,329 A | 1/1994 | Anderson ...................... 556/50 |
| 5,302,370 A | 4/1994 | Neumeier et al. ........... 424/1.53 |
| 5,328,913 A | * 7/1994 | Murad et al. |
| 5,393,903 A | 2/1995 | Grätzel et al. ................ 556/137 |
| 5,419,894 A | 5/1995 | Gries et al. ................... 424/1.65 |
| 5,424,057 A | 6/1995 | Peter et al. .................. 424/365 |
| 5,430,058 A | 7/1995 | Shanzer et al. ............... 514/575 |
| 5,430,164 A | 7/1995 | Abdel-Monem et al. ........ 556/2 |
| 5,474,931 A | 12/1995 | DiSorbo et al. ........ 435/240.31 |
| 5,480,894 A | 1/1996 | Hider et al. .................. 514/348 |
| 5,494,935 A | 2/1996 | Miller et al. .................. 514/674 |
| 5,506,266 A | 4/1996 | Davies et al. ................ 514/575 |
| 5,583,243 A | 12/1996 | Abdel-Monem ............. 556/49 |
| 5,624,901 A | 4/1997 | Raymond et al. ............. 514/17 |
| 5,637,311 A | 6/1997 | Pallenberg ................. 424/434 |
| 5,688,815 A | 11/1997 | Zbinden ..................... 514/348 |
| 5,707,604 A | 1/1998 | Ranney ..................... 424/9.35 |
| 5,746,995 A | 5/1998 | Maier et al. ................. 424/1.65 |
| 5,756,825 A | 5/1998 | Safavy et al. ................ 560/169 |
| 5,804,420 A | 9/1998 | Chan et al. ................. 435/69.6 |

FOREIGN PATENT DOCUMENTS

| | | |
|---|---|---|
| EP | 0 274 445 A2 | 7/1988 |
| EP | 0 282 942 A2 | 9/1988 |
| EP | 0 872 487 A2 | 10/1998 |
| EP | 0 872 487 A3 | 10/1999 |
| WO | WO 88/02774 | 4/1988 |
| WO | WO 93/00423 | 1/1993 |
| WO | WO 94/02592 | 2/1994 |
| WO | WO 97/34999 | 9/1997 |
| WO | WO 98/08934 | 3/1998 |
| WO | WO 98/15614 | 4/1998 |

OTHER PUBLICATIONS

Mostert et al., Free radical and cytotoxic effects of the chelators and their iron complexes in the hepatocyte (1987) Free Rad. Res. Commun., vol. 3, No. 6, pp. 379–399.*
Gibco Catalog, pp. 82, 83 (1992).*
Sun et al., "Structure and Behavior of Organic Analytical Reagents", Analytical Chemistry 36 (13) : 2485–88 (1964).*

(List continued on next page.)

*Primary Examiner*—Sandra E. Saucier
(74) *Attorney, Agent, or Firm*—Sterne, Kessler, Goldstein & Fox PLLC

(57) ABSTRACT

The present invention is directed generally to metal binding compounds which may be added to cell culture media to replace factors required for cultivation of the cells (e.g. transferrin) which are of animal or human origin. More specifically, the invention is directed to metal binding compounds or complexes thereof comprising one or more transition element cations (such as ferrous or ferric ions), which are added to cell and tissue culture medium compositions. The metal binding compounds may be added to the media alone or may be first complexed with a transition metal ion. The invention is also directed to methods of use of such compositions, including, for example, methods for the cultivation of eukaryotic cells, particularly animal cells, in vitro. The invention also relates to compositions comprising such culture media and one or more cells, and to kits comprising one or more of the above-described compositions. The compositions of the present invention obviate the need for naturally derived metal-binding proteins, such as transferrin and ceruloplasmin, which may contain blood-borne pathogens.

21 Claims, No Drawings

OTHER PUBLICATIONS

Landschulz et al., "A lipophilic iron chelator can replace transferrin as a stimulator of cell proliferation and differentiation", Journal of Cell Biology 98 : 596–601 (1984).*

Kontoghiorghes, "2–hydroxypyridine–N–oxides: effective new chelators in iron mobilisation", BBA 924 : 13–18 (1987).*

CA Registry No. 16867–04–2.*

CA Registry No. 2398–81–4.*

Chenoufi et al., "Inhibition of iron toxicity in rat and human hepatocyte cultures by the hydroxypyridin–4–ones CP20 and CP94", Journal of Hepatology 23 (2): 166–73 (1995).*

Gaut et al., "Uptake and metabolism of nicotinic acid by human blood platelets. Effects of structure analogs and metabolic inhibitors", Biochimica et Biophysica Acta 201(2), 316–22 (1970).*

Ward et al., "Inhibition of wool follicle DNA synthesis by mimosine and related 4(1H)–pyridones", Australian Journal of Biologica Sciences 29 (3) : 189–96 (1976).*

Bridges, K.R., and Cudkowicz, A., "Effect of Iron Chelators on the Transferrin Receptor in K562 Cells," *J. Biol. Chem.* 259:12970–12977, American Society of Biological Chemists, Inc. (1984).

Darfler, F.J., "A Protein–Free Medium for the Growth of Hybridomas and Other Cells of the Immune System," *In Vitro Cell. Dev. Biol.* 26:769–778, Tissue Culture Association (1990).

Eto, N., et al., "Development of a Protein–free Medium with Ferric Citrate Substituting Transferrin for the Cultivation of Mouse–Mouse Hybridomas," *Agric. Biol. Chem.* 55:863–865, Agricultural Chemical Society of Japan (1991).

Forsbeck, K., et al., "Variation in iron accumulation, transferrin membrane binding, and DNA synthesis in the K–562 and U–937 cell lines induced by chelators and their iron complexes," *Eur. J. Haemotol.* 39:318–325, Munksgard (1987).

Ganeshaguru, K., et al., "Effect of Various Iron Chelating Agents on DNA Synthesis in Human Cells," *Biochem. Pharmacol.* 29:1275–1279, Pergamon Press Ltd. (1980).

Ham, R.G., "Formulation of Basal Nutrient Media," in *Methods for Preparation of Media, Supplements and Substrata for Serum–Free Animal Cell Culture,* vol. 1, Barnes, D.W., et al., eds., Alan R. Liss, Inc., New York, pp. 3–21 (1984).

Inoue, Y., et al., "Production of Recombinant Human Monoclonal Antibody Using ras–Amplified BHK–21 Cells in a Protein–free Medium," *Biosci. Biotech. Biochem.* 60:811–817, Japan Society for Bioscience, Biotechnology, and Agrochemistry (1996).

Keenan, J., and Clynes, M., "Replacement of Transferrin by Simple Iron Compounds for MDCK Cells Grown and Subcultured in Serum–Free Medium," *In Vitro Cell Dev. Biol.— Animal* 32:451–453, Society for In Vitro Biology (1996).

Kontoghiorghes, G.J., "The study of iron mobilisation from transferrin using α–ketohydroxy heteroaromatic chelators," *Biochem. Biophys. Acta* 869:141–146, Elsevier Science Publishers B.V. (1986).

Koller, M.R., et al., "Alternatives to Animal Sera for Human Bone Marrow Cell Expansion: Human Serum and Serum–Free Media," *J. Haematotherapy* 7:413–423, Mary Ann Liebert, Inc. (Oct. 1998).

Korohoda, W., et al., "Addition of iron and zinc complexes to Eagle's Minimal Essential Medium is sufficient to induce and support the proliferation of B16 melanoma cells," *Folia Histochemica et Cytobiologica* 31:3–7, Polish Histochemical And Cytochemical Society And Foundation For Cell And Molecular Biology At Vesalius University Medical Publisher (1993).

Nagira, K., et al., "Development of a Protein–free Medium with Iron Salts Replacing Transferrin for a Human–Human Hybridoma," *Biosci. Biotech. Biochem.* 59:743–745, Japan Society for Bioscience, Biotechnology, and Agrochemistry (1995).

Neumannova, V., et al., "Growth of Human Tumor Cell Lines in Transferrin–Free, Low–Iron Medium," *In Vitro Cell. Dev. Biol.—Animal* 31:625–632, Society for In Vitro Biology (1995).

Okabe, T., et al., "Long–term cultivation and differentiation of human erythroleukemia cells in a protein–free chemically defined medium," *Proc. Natl. Acad. Sci. USA* 81:453–455, National Academy of Sciences of the USA (1984).

Qian, Z.M. and Tang, P.L., "Mechanisms of iron uptake by mammalian cells," *Biochim. Biophys. Acta* 1269:205–214, Elsevier Science B.V. (1995).

Rivkin, G., et al., "IRC011, a New Synthetic Chelator With Selective Interaction With Catabolic Red Blood Cell Iron: Evaluation in Hypertransfused Rats With Hepatocellular and Reticuloendothelial Radioiron Probes and in Iron–Loaded Rat Heart Cells in Culture," *Blood* 90:4180–4187, W. B. Saunders (1997).

Schneider, Y.–J., "Optimisation of hybridoma cell growth and monoclonal antibody secretion in a chemically defined, serum– and protein–free culture medium," *J. Immunol. Meth.* 116:65–77, Elsevier Science Publishers B.V. (1989).

Testa, U., et al., "The iron–chelating agent picolinic acid enhances transferring receptors expression in human erythroleukaemic cell lines," *Brit. J. Haematol.* 60:491–502, Blackwell Science Ltd. (1985).

Waymouth, C., "Preparation and Use of Serum–Free Culture Media," in *Methods for Preparation of Media, Supplements and Substrata for Serum–Free Animal Culture,* vol. 2, Barnes, D.W., et al., eds., Alan. R. Liss, Inc., New York, pp. 23–68 (1984).

White, G.P., et al., "The Effect of Chelating Agents on Iron Mobilization in Chang Cell Cultures," *Blood* 48:923–929, W.B. Saunders (1976).

Yabe, N., et al., "Role of Iron Chelators in Growth–Promoting Effect on Mouse Hybridoma Cells in a Chemically Defined Medium," *In Vitro Cell. Dev. Biol.* 23:815–820, Tissue Culture Association, Inc. (1987).

Yabe, N., and Matsui, H., "Effects of Iron Chelates on the Transferrin–Free Culture of Rat Dermal Fibroblasts Through Active Oxygen Generation," *In Vitro Cell. Dev. Biol.–Animal* 33:527–535, Society for In Vitro Biology (1997).

Zang, M., et al., "Production of Recombinant Proteins in Chinese Hamster Ovary Cells Using A Protein–Free Cell Culture Medium," *Bio/Technol.* 13:389–392, Nature Publishing Co. (1995).

Kriegerbecková, K., et al., "Non–Transferrin Iron Uptake by HeLa Cells Cultured in Serum–Free Media with Different Iron Sources," *Eur. J. Clin. Chem. Clin. Biochem.* 33:791–797, Walter de Gruyter & Co. (1995).

International Search Report for International Patent No. PCT/US00/23580, mailed Mar. 28, 2001.

* cited by examiner

METAL BINDING COMPOUNDS AND THEIR USE IN CELL CULTURE MEDIUM COMPOSITIONS

CROSS REFERENCE TO RELATED APPLICATION

The present application claims the benefit of U.S. Provisional Application No. 60/151,055 filed Aug. 27, 1999, the contents of which are fully incorporated by reference herein.

BACKGROUND OF THE INVENTION

1. Field of the Invention

The present invention is in the fields of cell biology and biochemistry. The invention relates generally to cell and tissue culture medium compositions comprising metal binding compounds and/or transition element complexes comprising the metal binding compounds, and the use of such compounds and complexes. More specifically, the invention relates to compositions for cell and tissue culture comprising one or more transition element cations in a complex with a metal binding compound.

2. Related Art

Cell culture media provide the nutrients necessary to maintain and grow cells in a controlled, artificial and in vitro environment. Characteristics and formulations of cell culture media vary depending upon the particular cellular requirements. Important parameters include osmolarity, pH, and nutrient compositions.

Medium formulations have been used to cultivate a number of cell types including animal, plant and bacterial cells. Cultivated cells have many uses including the study of physiological processes and the production of useful biological substances. Examples of such useful products include monoclonal antibodies, hormones, growth factors, enzymes and the like. Such products have many commercial and therapeutic applications and, with the advent of recombinant DNA technology, cells can be engineered to produce large quantities of these products. Cultured cells are also routinely used for the isolation, identification and growth of viruses which may be used as vectors and/or vaccines. Thus, the ability to cultivate cells in vitro is not only important for the study of cell physiology, but is also necessary for the production of useful substances which may not otherwise be obtained by cost-effective means.

Cell culture medium formulations have been well documented in the literature and a number of media are commercially available. In early cell culture work, medium formulations were based upon the chemical composition and physicochemical properties (e.g., osmolality, pH, etc.) of blood and were referred to as "physiological solutions" (Ringer, S., J. Physiol., 3:380–393 (1880); Waymouth, C., In: Cells and Tissues in Culture, Vol. 1, Academic Press, London, pp. 99–142 (1965);Waymouth, C., In Vitro 6:109–127 (1970)). However, cells in different tissues of the mammalian body are exposed to different microenvironments with respect to oxygen/carbon dioxide partial pressure and concentrations of nutrients, vitamins, and trace elements; accordingly, successful in vitro culture of different cell types may require the use of different medium formulations. Typical components of cell culture media include amino acids, organic and inorganic salts, vitamins, trace metals, sugars, lipids and nucleic acids, the types and amounts of which may vary depending upon the particular requirements of a given cell or tissue type.

Typically, cell culture medium formulations are supplemented with a range of additives, including undefined components such as fetal bovine serum (FBS) (10–20% v/v) or extracts from animal embryos, organs or glands (0.5–10% v/v). While FBS is the most commonly applied supplement in animal cell culture media, other serum sources are also routinely used, including newborn calf, horse and human. These types of chemically undefined supplements serve several useful functions in cell culture media (Lambert, K. J. et al., In: Animal Cell Biotechnology, Vol. 1, Spier, R. E. et al., Eds., Academic Press New York, pp. 85–122 (1985)). For example, these supplements provide carriers or chelators for labile or water-insoluble nutrients; bind and neutralize toxic moieties; provide hormones and growth factors, protease inhibitors and essential, often unidentified or undefined low molecular weight nutrients; protect cells from physical stress and damage; and provide carriers (e.g., transferrin and ceruloplasmin) for certain essential metal ions (e.g., $Fe^{++}$ and $Fe^{+++}$). Thus, serum and/or animal extracts are commonly used as relatively low-cost supplements to provide an optimal culture medium for the cultivation of animal cells.

Unfortunately, the use of serum or animal extracts in tissue culture applications has several drawbacks (Lambert, K. J. et al., In: Animal Cell Biotechnology, Vol 1, Spier, R. E. et al., Eds., Academic Prcs New York, pp. 85–122 (1985)). For example, the chemical composition of these supplements may vary between lots, even from a single manufacturer. In addition, supplements of animal or human origin may also be contaminated with adventitious agents (e.g., mycoplasma, viruses, and prions). These agents can seriously undermine the health of the cultured cells when these contaminated supplements are used in cell culture media formulations. Further, these agents may pose a health risk when substances produced in cultures contaminated with adventitious agents are used in cell therapy and other clinical applications. A major fear is the presence of prions which cause spongiform encephalopathies in animals and Creutzfeld-Jakob disease in humans.

The presence of serum in culture media can present additional difficulties. Cell surface chemistry, which is a critical portion of the in vitro microenvironment for many cell types, can be adversely modified via adsorption or incorporation of serum or extract proteins. The use of undefined components such as serum or animal extracts also prevents the true definition and elucidation of the nutritional and hormonal requirements of the cultured cells, thus eliminating the ability to study, in a controlled way, the effect of specific growth factors or nutrients on cell growth and differentiation in culture. Moreover, undefined supplements prevent the researcher from studying aberrant growth and differentiation and specific disease-related changes in cultured cells. Using cell culture media in the industrial production of biological substances, serum and animal extract supplementation of culture media can also complicate and increase the costs of the purification of the desired substances from the culture media due to the necessity of removing serum or extract proteins.

Serum-Free Media

To overcome the drawbacks of the use of serum or animal extracts, a number of serum-free media have been developed. These media, which often are specifically formulated to support the culture of a single cell type, incorporate defined quantities of purified growth factors, lipoproteins and other proteins usually provided by the serum or extract supplement. Since the components (and concentrations thereof) in such culture media are precisely known, these media arc generally referred to as "defined culture media" and often as "serum-free media" or "SFM." A number of SFM formulations are commercially available from, for example, Life Technologies, Inc. (Rockville, Md.) such as those designed to support the culture of endothelial cells, keratinocytes, monocytes/macrophages, fibroblasts, neurons, lymphocytes, chondrocytes, hematopoietic stem cells, embryonic stem cells, insect cells, CHO cells, Vero cells, 293 HEK cells, HeLa cells, PER-C6 (Human embryonal retinal epithelial cells), or hepatocytes.

SFM generally provide several distinct advantages to the user. For example, the use of SFM facilitates the investigation of the effects of a specific growth factor or other medium component on cellular physiology, which may be masked when the cells are cultivated in serum- or extract-containing media. In addition, SFM may contain much lower quantities of protein (indeed, SFM are often termed "low protein media") than those containing serum or extracts, greatly simplifying and lowering the cost of purifying biological substances produced by cells cultured in SFM.

Some extremely simple SFM, which consist essentially of vitamins, amino acids, organic and inorganic salts and buffers have been used for cell culture. Such media (often called "basal media"), however, are usually seriously deficient in the nutrition, hormone, or biological response modifier content required by most animal cells. Accordingly, most SFM incorporate into the basal media additional components to make the media more nutritionally or hormonally complex while attempting to maintain the serum-free and low protein content nature of the media. Examples of such components include serum albumin from bovine (BSA) or human (HSA), animal-derived lipids such as human Excyte (Bayer); sterols, etc., insulin, transferrin, and certain growth factors or hormones derived from natural (animal) or recombinant sources.

The use of such animal-derived supplements in cell culture media, however, also has certain drawbacks. For example, there is a risk that the culture medium and/or products purified from it may be immunogenic, particularly if the supplements are derived from an animal different from the source of the cells to be cultured. Thus, if biological substances to be used as therapeutics are purified from such culture media, certain amounts of these immunogenic proteins or peptides may be co-purified and may induce an immunological reaction, up to and including anaphylaxis, in an animal receiving such therapeutics.

To overcome this potential problem, supplements derived from the same species as the cells to be cultured may be used. For example, culture of human cells may be facilitated using HSA as a supplement, while media for the culture of bovine cells would instead use BSA. This approach, however, runs the risks of introducing contaminants and adventitious pathogens into the culture medium (such as HIV, Creutzfeld Jakob agent, or hepatitis viruses from HSA preparations, or Bovine Spongiform Encephalopathy prion from BSA preparations), which can obviously negatively impact the use of such media in the preparation of animal and human therapeutics. In fact, for such safety reasons, the biotechnology industry and government agencies are increasingly regulating, discouraging and even forbidding the use of cell culture media containing human or animal-derived products which may contain such pathogens.

Nothwithstanding the potential difficulties posed by the addition of animal derived supplements to cell culture media, such supplements are in routine use. One such supplement that is frequently added to defined media is transferrin. Transferrin functions in vivo to deliver iron to cells. The mechanism of iron uptake by mammalian cells has been reviewed (Qian, Z. M. and Tang, P. L. (1995) Biochim.Biophys.Acta 1269, 205–214). As iron is required as a co-factor in numerous metabolic processes including energy generation and oxidative respiration, serum-free media are often supplemented with transferrin in order to deliver the requisite iron for the successful cultivation of most cells in vitro. Concern about various potential adventitious agents in preparations of transferrin has stimulated a search for other natural iron carrier compounds which can be used as a substitute for transferrin. This search is complicated by the fact that the natural iron carriers are often derived from serum and thus are subject to the above-described limitations of serum supplementation.

Metal Binding Compounds

To overcome the limitations of using naturally derived metal carriers, certain metal binding compounds are being explored for use in supplying metals, particularly zinc, iron, manganese and magnesium, to cultured cells. Simple carriers such as chelating agents (e.g., EDTA) and certain acids or salts thereof (e.g., citrate, picolinate, and derivatives of benzoic acid or hydroxamic acid) have been shown to be useful in certain serum-free growth media (see U.S. Pat. Nos. 5,045,454 and 5,118,513; Testa et al., *Brit. J. Haematol.* 60:491–502, (1985); Ganeshaguru et al., *Biochem. Pharmacol.* 29:1275–1279 (1980); White et al., *Blood* 48:923–929 (1976)).

Although these references disclose some metal carriers, the interpretation of the data is complicated by several experimental factors. The data were gathered from a limited number of cell lines and show results of a single passage. In addition, the media were supplemented with serum. Serum inherently contains transferrin and other potential iron carriers. There is a "carry-over effect" on growth of cells which have been cultured in serum-supplemented medium, even after one or two passages in the absence of serum or transferrin (see, for example, Keenan, J. and Clynes, M. (1996) In Vitro Cell Dev.Biol-Animal 32, 451–453). Other known metal binding compounds have been used medicinally to remove iron from the body and not for delivery. Unfortunately, many of these simple iron chelating compounds do not provide sufficient iron availability to, or uptake by, cultured cells.

Thus, there remains a need in the art for compounds capable of delivering transition metals to cells cultured in vitro. More specifically, there exists a need in the art for iron carriers for use in serum-free, low-protein culture medium which are suitable for cultivation of eukaryotic and prokaryotic cells. Such a medium formulation will facilitate studies of the effects of growth factors and other stimuli on cellular physiology, will allow easier and more cost-effective purification of biological substances produced by cultured animal cells in the biotechnology industry, and most importantly will eliminate the risk of the introduction of adventitious animal and human pathogens. The current invention provides such a variety of compounds or specifically iron carriers for an animal cell culture medium formulation.

BRIEF SUMMARY OF THE INVENTION

The present invention meets the need in the art for compounds capable of delivering transition metals to cells cultured in vitro by providing culture media that comprise one or more non-animal-derived metal-binding compounds which may be used to provide essential metals (e.g., $Fe^{++}$ or $Fe^{+++}$ ions) to cells. The compounds provided by the invention comprise a metal binding compound which may be added to a medium alone or may be complexed with one or more transition element ions prior to addition to the medium.

The compounds described herein were used to facilitate the delivery of transition metals to cells cultured in vitro. In particular, the compounds of the present invention were selected for their ability to deliver iron and to replace transferrin. The compounds were tested in the absence of transferrin for at least three sub-cultures. These compounds have been tested for their ability to support the growth of at least three commonly used cell lines: CHO, Sp2/0, and 293 HEK cells.

The present invention is also directed to compositions, particularly cell culture media, comprising one or more metal binding compounds of the invention and/or one or more transition elements in a complex with one or more metal binding compounds of the invention. Such cell culture media of the invention may be used to grow or cultivate plant cells, animal cells (particularly human cells), insect cells, bacterial cells, yeast cells and more generally any type of eukaryotic or prokaryotic cells. Thus, the metal binding compounds of the present invention may be added to any type or kind of culture media, and are preferably used to replace naturally derived metal carriers (e.g., animal derived proteins or extracts such as transferrin) in such media. The invention is also directed to methods of use of such compositions, including, for example, methods for the cultivation of eukaryotic cells, particularly animal cells, in vitro. The invention also relates to compositions comprising such culture media and one or more cells, and to kits comprising one or more of the above-described compositions.

Culture media of the invention are preferably serum-free, and may comprise at least one metal binding compound and/or at least one transition element complex, said complex comprising at least one transition element or a salt or ion thereof, in a complex with at least one metal-binding compound, wherein the medium is capable of supporting the cultivation of a cell in vitro in the absence of naturally derived metal carriers such as transferrin or other animal derived proteins or extracts. The metal binding compound may be in a complex with a transition metal prior to addition of the metal binding compound to the medium. In other embodiments, the metal binding compound is not in a complex with a transition metal prior to addition of the metal binding compound to the media.

According to one aspect of the invention, a transition element is preferably selected from the group consisting of scandium, titanium, vanadium, chromium, manganese, iron, cobalt, nickel, copper, zinc, yttrium, zirconium, niobium, molybdenum, technetium, rubidium, rhodium, palladium, silver, cadmium, lanthanum, hafnium, tantalum, tungsten, rhenium, osmium, iridium, platinum, gold, mercury, and actinium, or salts or ions thereof, and is preferably an iron salt. Suitable iron salts include, but are not limited to, $FeCl_3$, $Fe(NO_3)_3$ or $FeSO_4$ or other compounds that contain $Fe^{+++}$ or $Fe^{++}$ ions.

Metal binding compounds of the present invention include any molecules which may interact with or bind with transition elements and facilitate the uptake by cells. Such interaction/binding may be covalent or non-covalent in nature. The metal-binding compound used in this aspect of the invention is preferably selected from the group consisting of a polyol, a hydroxypyridine derivative, 1,3,5-N,N', N''-tris(2,3-dihydroxybenzoyl)aminomethylbenzene, ethylenediamine-N,N'-tetramethylenephosphonic acid, trisuccin, an acidic saccharide (e.g. ferrous gluconate), a glycosaminoglycan, diethylenetriaminepentaacetic acid, nicotinic acid-N-oxide, 2-hydroxy-nicotinic acid, mono-, bis-, or tris-substituted 2,2'-bipyridine, a hydroxamate derivative (e.g. acetohydroxamic acid), an amino acid derivative, deferoxamine, ferrioxamine, iron basic porphine and derivatives thereof, DOTA-lysine, a texaphyrin, a sapphyrin, a polyaminocarboxylic acid, an α-hydroxycarboxylic acid, a polyethylenecarbamate, ethyl maltol, 3-hydroxy-2-pyridine, and IRC011. In one preferred embodiment, the metal-binding compound is a polyol such as sorbitol or dextran, and particularly sorbitol. In a related embodiment, the metal-binding compound is a hydroxypyridine derivative, such as 2-hydroxypyridine-N-oxide, 3-hydroxy-4-pyrone, 3-hydroxypypyrid-2-one, 3-hydroxypyrid-2-one, 3-hydroxypyrid4-one, 1-hydroxypyrid-2-one, 1,2-dimethyl-3-hydroxypyrid-4one, 1-methyl-3-hydroxypyrid-2-one, (3-hydroxy-2(1H)-pyridinone, ethyl maltol or pyridoxal isonicotinyl hydrazone, and is preferably 2-hydroxypyridine-N-oxide. In particularly preferred embodiments according to this aspect of the invention, the transition metal complex may be a sorbitol-iron complex or 2-hydroxypyridine-N-oxide-iron complex. The metal binding compounds of the present invention may also bind divalent cations such as $Ca^{++}$ and $Mg^{++}$.

In a related aspect, the invention relates to cell culture media comprising at least one metal binding compound capable of binding or interacting with one or more transition elements and further comprising one or more ingredients selected from the group of ingredients consisting of at least one amino acid (such as L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine or L-valine, N-acetyl-cysteine), at least one vitamin (such as biotin, choline chloride, D-$Ca^{++}$-pantothenate, folic acid, i-inositol, niacinamide, pyridoxine, riboflavin, thiamine or vitamin $B_{12}$), at least one inorganic salt (such as a calcium salt, $CuSO_4$, $FeSO_4$, $Fe(NO_3)_3$, $FeCl_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt or a zinc salt), adenine, ethanolamine, D-glucose, at least one cytokine, heparin, hydrocortisone, lipoic acid, phenol red, phosphoethanolamine, putrescine, sodium pyruvate, tri-iodothyronine, dextran sulfate, Pluronic F68, and thymidine. The culture media of the present invention may optionally include a buffeting agent. Suitable buffering agents include, but are not limited to, N-[2-hydroxyethyl]-piperazine-N'-[2-ethanesulfonic acid] (HEPES), MOPS, MES, phosphate, carbonate and other buffering agents suitable for use in cell culture applications. A suitable buffering agent is one that provides buffering capacity without substantial cytotoxicity to the cells cultured. The selection of suitable buffering agents is within the ambit of ordinary skill in the art of cell culture.

In another aspect, the invention relates to a metal binding compound capable of binding a transition element in a cell culture medium comprising one or more of the ingredients selected from the group: adenine, ethanolamine, D-glucose, N-[2-hydroxyethyl]piperazine-N'-[2-ethanesulfonic acid] (HEPES), hydrocortisone, lipoic acid, phenol red, phosphoethanolamine, putrescine, sodium pyruvate, tri-iodothyronine, thymidine, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, N-acetyl-cysteine, biotin, choline chloride, D-$Ca^{++}$- pantothenate, folic acid, i-inositol, niacinamide, pyridoxine, riboflavin, thiamine, vitamin $B_{12}$, a calcium salt, recombinant insulin, dextran sulfate, Pluronic F68, $CuSO_4$, $FeSO_4$, $FeCl_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, and a zinc salt, and one or more transition element complexes comprising at least one transition element or a salt or ion thereof complexed to at least one metal-binding compound, wherein each ingredient is present in an amount which supports the cultivation of a cell in vitro. Preferred transition elements, metal-binding compounds, and transition element complexes for use in this aspect of the invention include those described in detail herein.

In another aspect, the invention relates to a cell culture medium obtained by combining a medium with at least one metal binding compound and/or at least one transition element complex, said complex comprising at least one transition element or a salt or ion thereof complexed to at least one metal-binding compound, wherein said medium is capable of supporting the cultivation of a cell in vitro. Preferred transition elements, metal-binding compounds, and transition element complexes for use in this aspect of the invention include those described in detail herein.

According to the invention, a medium suitable for use in forming the cell culture media of the invention may comprise one or more ingredients, and may be obtained, for example, by combining one or more ingredients selected from the group consisting of adenine, ethanolamine, D-glucose, heparin, a buffering agent, hydrocortisone, lipoic acid, phenol red, phosphoethanolamine, putrescine, sodium pyruvate, tri-iodothyronine, thymidine, L-alanine, L-arginine, L-asparagine, L-aspartic acid, Lysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, N-acetyl-cysteine, biotin, choline chloride, $D-Ca^{++}$-pantothenate, folic acid, i-inositol, niacinamide, pyridoxine, riboflavin, thiamine, vitamin $B_{12}$, dextran sulfate, Pluronic F68, recombinant insulin, a calcium salt, $CuSO_4$, $FeSO_4$, $FeCl_3$, $Fe(NO_3)_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt and a zinc salt, wherein each ingredient is added in an amount which supports the cultivation of a cell in vitro.

According to the invention, the culture media provided by or obtained by the invention may be 1×medium formulations, or may be concentrated medium formulations, for example 10×, 20×, 25×, 50×, 100×, 500×, or 1000× medium formulations.

Both eukaryotic and prokaryotic cells may be cultivated in the media provided or obtained by the invention, including but not limited to mammalian cells (including human cells), bird cells, insect cells, fish cells, amphibian cells, and reptile cells, any or all of which may be normal cells or abnormal cells (such as transformed cells, established cells, or a cells derived from a diseased tissue sample). Cells may also include plant cells or microbial cells such as bacteria and lower eukaryotic cells such as fungi and yeast.

In another aspect, the invention relates to methods of cultivating cells, such as those cells described above, comprising (a) contacting the cell with the cell culture media of the invention; and (b) cultivating the cell under conditions suitable to support cultivation or growth of the cell.

In another aspect, the invention relates to kits for the cultivation of a cell in vitro. Kits according to one such aspect of the invention may comprise one or more of the culture media of the invention, one or more metal binding compounds, and/or one or more transition element complexes. Kits according to another aspect of the invention may comprise one or more cell culture media (one of which may be a basal medium) and at least one metal binding compound and/or at least one transition element complex, said complex comprising at least one transition element or a salt or ion thereof complexed to at least one metal-binding compound. Preferred transition elements, metal-binding compounds, and transition element complexes for use in the kits according to this aspect of the invention include those described in detail herein.

In another aspect, the invention relates to compositions comprising the culture media of the invention and one or more cells, including those cells described above.

Other preferred embodiments of the present invention will be apparent to one of ordinary skill in light of the following drawings and description of the invention, and of the claims.

DETAILED DESCRIPTION OF THE INVENTION

The present invention provides a supplement to medium formulations for the growth of both eukaryotic and prokaryotic cells. Such a supplement may replace certain ingredients of a medium formulation. Preferably, such a supplement may replace components derived from biological sources, eg. animal sources, plant sources, bacterial sources, etc. In a preferred aspect, components replaced by one or more metal binding compounds of the present invention include, but are not limited to, proteins, cell or tissue extracts, serum lipids, growth factors and the like. The compounds of the present invention can be used to support or enhance the growth in culture of any cell that requires transition metals to support growth.

Definitions

In the description that follows, a number of terms conventionally used in the fields of cell biology and cell culture media are utilized extensively. In order to provide a clear and consistent understanding of the specification and claims, and the scope to be given such terms, the following definitions are provided.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "cell" as used herein is seen to include all types of eukaryotic and prokaryotic cells.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

By "cultivation" is meant the maintenance of cells in vitro under conditions favoring growth, differentiation or continued viability, in an active or quiescent state, of the cells. In this sense, "cultivation" may be used interchangeably with "cell culture" or any of its synonyms described above.

By "culture vessel" is meant a glass, plastic, or metal container that can provide an aseptic environment for culturing cells.

The phrases "cell culture medium," "tissue culture medium," "culture medium" (plural "media" in each case) and "medium formulation" refer to a nutritive solution for cultivating cells or tissues, and may be used interchangeably.

The metal binding compounds of the present invention and/or transition metal complexes formed with the metal binding compounds of the present invention may be use with any media, including media for cultivating or growing eukaryotic and/or prokaryotic cells, tissues, organs, etc. Such media include, but. are not limited to, Dulbecco's Modified Eagle's Medium (DMEM), Minimal Essential Medium (MEM), Basal Medium Eagle (BME), RPMI-1640, Ham's F-10, Ham's F-12, αMinimal Essential Medium (αMEM), Glasgow's Minimal Essential Medium (G-MEM), and Iscove's Modified Dulbecco's Medium (IMDM). Other media that are commercially available (e.g., from Life Technologies, Inc.; Rockville, Md. or that are otherwise known in the art may be equivalently used in accordance with the present invention including, but not limited to, 293 SFM, CD-CHO medium, VP SFM, BGJb medium, Brinster's BMOC-3 medium, cell culture freezing medium, CMRL media, EHAA medium, eRDF medium, Fischer's medium, Gamborg's B-5 medium, GLUTAMAX™ media, Grace's insect cell media, HEPES media, Richter's modified MEM, IPL-41 insect cell medium, Leibovitz's L-15 media, McCoy's 5A media, MCDB 131 medium, Media 199, Modified Eagle's Medium (MEM), Medium NCTC-109, Schneider's Drosophila medium, TC-100 insect medium, Waymouth's MB 752/1 media, William's Media E, protein free hybridoma medium II (PFHM II), AIM V media, Keratinocyte SFM, defined Keratinocyte SFM, STEMPRO® SFM, STEMPRO® complete methylcellulose medium, HepatoZYME-SFM, Neurobasal™ medium, Nerobasal-A medium, Hibernate™ A medium, Hibernate E medium, Endothelial SFM, Human Endothelial SFM, Hybridoma SFM, PFHM II, Sf 900 medium, Sf 900 II SFM, EXPRESS FIVE® medium, CHO-S-SFM, AMINOMAX-II complete medium, AMINOMAX-C100 complete medium, AMINOMAX-C100 basal medium, PB-MAX™ karyotyping medium, KARYOMAX bone marrow karyotyping medium, KNOCKOUT D-MEM and $CO_2$ independent medium. Additional examples of media suitable for use in the practice of the present invention may be found in U.S. Pat. Nos. 5,135,866 and 5,232,848 as well as in international publications nos. WO 88/02774, WO 98/15614, WO 98/08934 and European patent no. 0 282 942 all of which are specifically incorporated herein by reference.

The term "contacting" refers to the placing of cells to be cultivated in vitro into a culture vessel with the medium in which the cells are to be cultivated. The term "contacting" encompasses mixing cells with medium, pipetting medium onto cells in a culture vessel, and submerging cells in culture medium.

The term "combining" refers to the mixing or admixing of ingredients in a cell culture medium formulation.

A cell culture medium is composed of a number of ingredients and these ingredients vary from medium to medium. Each ingredient used in a cell culture medium has unique physical and chemical characteristics. Compatibility and stability of ingredients are determined by the "solubility" of the ingredients in aqueous solution. The terms "solubility" and "soluble" refer to the ability of an ingredient to form a solution with other ingredients. Ingredients are thus compatible if they can be maintained in solution without forming a measurable or detectable precipitate. Thus, the term "compatible ingredients" as used herein refers to the combination of particular culture media ingredients which, when mixed in solution either as concentrated or 1×formulations, are "stable" and "soluble."

By "compatible ingredients" is also meant those media nutrients which can be maintained together in solution and form a "stable" combination. A solution containing "compatible ingredients" is said to be "stable" when the ingredents do not precipitate, degrade or decompose substantially such that the concentration of one or more of the components available to the cells from the media is reduced to a level that no longer supports the optimum growth of the cells. Ingredients are also considered "stable" if degradation cannot be detected or when degradation occurs at a slower rate when compared to decomposition of the same ingredient in a 1×cell culture media formulation. For example, in 1×media formulations glutamine is known to degrade into pyrolidone carboxylic acid and ammonia. Glutamine in combination with divalent cations are considered "compatible ingredients" since little or no decomposition of the glutamine can be detected over time in solutions or combinations in which both glutamine and divalent cations are present. See U.S. Pat. No. 5,474,931. It has been demonstrated by the inventors that in addition to stabilizing glutamine, glutamine complexed with $FeCl_3$ can be substituted for transferrin.

The term "1×formulation" is meant to refer to any aqueous solution that contains some or all ingredients found in a cell culture medium at working concentrations. The "1×formulation" can refer to, for example, the cell culture medium or to any subgroup of ingredients for that medium. The concentration of an ingredient in a 1×solution is about the same as the concentration of that ingredient found in a cell culture formulation used for maintaining or cultivating cells in vitro. A cell culture medium used for the in vitro cultivation of cells is a 1×formulation by definition. When a number of ingredients are present, each ingredient in a 1×formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic acid. A "1×formulation" of these amino acids contains about the same concentrations of these ingredients in solution. Thus, when referring to a "1×formulation," it is intended that each ingredient in solution has the same or about the same concentration as that found in the cell culture medium being described. The concentrations of ingredients in a 1×formulation of cell culture medium are well known to those of ordinary skill in the art. See, for example, *Methods For Preparation of Media, Supplements and Substrate For Serum-Free Animal Cell Culture* Allen R. Liss, N.Y. (1984), *Handbook of Microbiological Media,* Second Ed., Ronald M. Atlas, ed. Lawrence C. Parks (1997) CRC Press, Boca Raton, Fla. and *Plant Culture Media,* Vol. 1: Formulations and Uses E. F. George, D. J. M. Puttock, and H. J. George (1987) Exegetics Ltd. Edington, Westbury, Wilts, BA13 4QG England each of which is incorporated by reference herein in its entirety. The osmolarity and/or pH, however, may differ in a 1×formulation compared to the culture medium, particularly when fewer ingredients are contained in the 1×formulation.

A "10×formulation" is meant to refer to a solution wherein each ingredient in that solution is about 10 times more concentrated than the same ingredient in the cell culture medium. For example, a 10×formulation of RPMI-1640 culture medium may contain, among other ingredients, 2.0 g/L L-arginine, 0.5 g/L L-asparagine, and 0.2 g/L L-aspartic acid (compare 1×formulation, above). A "10× formulation" may contain a number of additional ingredients at a concentration about 10 times that found in the 1×culture medium. As will be readily apparent, "25×formulation," "50×formulation," "100×formulation," "500×formulation," and "1000×formulation" designate solutions that contain ingredients at about 25-, 50-, 100-, 500-, or 1000-fold concentrations, respectively, as compared to a 1×cell culture medium. Again, the osmolarity and pH of the media formulation and concentrated solution may vary.

The term "trace element" or "trace element moiety" refers to a moiety which is present in a cell culture medium in only very low (i.e., "trace") amounts or concentrations, relative to the amounts or concentrations of other moieties or components present in the culture medium. In the present invention, these terms encompass $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$ and $Zr^{4+}$ and salts thereof. For example, the following salts can be used as trace elements in the culture media of the invention: $AgNO_3$, $AlCl_3.6H_2O$, $Ba(C_2H_3O_2)_2$, $CdSO_4.8H_2O$, $CoCl_2.6H_2O$, $Cr_2(SO_4)_3.1H_2O$, $GeO_2$, $Na_2SeO_3$, $H_2SeO_3$ KBr, KI, $MnCl_2.4H_2O$, NaF, $Na_2SiO_3.9H_2O$, $NaVO_3$, $(NH_4)_6Mo_7O_{24}.4H_2O$, $NiSO_4.6H_2O$, RbCl, $SnCl_2$, and $ZrOCl_2.8H_2O$. Suitable concentrations of trace element moieties can be determined by one of ordinary skill in the art using only routine experimentation.

The term "amino acid" refers to amino acids or their derivatives (e.g., amino acid analogs), as well as their D- and L-forms. Examples of such amino acids include glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine, N-acetyl cysteine.

A "serum-free" medium is a medium that contains no serum (e.g., fetal bovine serum (FBS), calf serum, horse serum, goat serum, human serum, etc.) and is generally designated by the letters SFM.

The terms "serum-free culture conditions" and "serum-free conditions" refer to cell culture conditions that exclude serum of any type and may be used interchangeably.

The phrase "protein-free" culture media refers to culture media that contain no protein (e.g., no serum proteins such as serum albumin or attachment factors, nutritive proteins such as growth factors, or metal ion carrier proteins such as transferrin, ceruloplasmin, etc.). The phrase "low-protein" culture media as used herein refers to media that contain only low amounts of protein (typically less than about 10%, less than about 5%, less than about 1%, less than about 0.5%, or less than about 0.1%, of the amount or concentration of total protein found in culture media containing standard amounts of protein, such as standard basal medium supplemented with 5–10% serum).

By "transition element" or "transition metal" (which may be used interchangeably) is meant an element in which an inner electron valence shell, rather than an outer shell, is only partially filled, such that the element acts as a transitional link between the most and least electropositive in a given series of elements. Transition elements are typically characterized by high melting points, high densities, high dipole or magnetic moments, multiple valencies, and the ability to form stable complex ions. Examples of such transition elements include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), rubidium (Ru), rhodium (Rh), palladium (Pd), silver (Ag), cadmium (Cd), lanthanum (La), hafnium (Hf), tantalum (Ta), tungsten (W), rhenium (Re), osmium (Os), iridium (Ir), platinum (Pt), gold (Au), mercury (Hg), and actinium (Ac). Of particular interest as a transition element for use in culture media compositions, including those of the present invention, are ions, chelates, salts, and complexes of iron ($Fe^{++}$ or $Fe^{+++}$).

Overview

The present invention relates generally to cell and tissue culture medium compositions comprising one or more metal binding compounds and/or one or more transition element complexes comprising the metal binding compounds. Further, the invention relates to the use of such culture media compositions in the cultivation of a variety of cells in vitro. One aspect of the present invention relates to cell and tissue culture compositions comprising one or more metal binding compounds transition element cations, particularly one or more multivalent transition element cations (such as $Fe^{++}$ or $Fe^{+++}$ ions), that are required for metabolic processes in living organisms. The compositions provided by the invention may comprise one or more transition element ions complexed with one or more non-protein metal-binding compounds. The invention also relates to methods for cultivating cells, particularly one or more animal cells including mammalian (e.g., human) cells, comprising contacting the cells with one or more of the culture media of the invention. The invention also relates to compositions comprising the culture media of the invention and one or more cells, and to kits comprising one or more of the compositions or culture media of the invention.

The compounds of the present invention are capable of supporting the growth of cells through multiple passages. This is relevant because those compounds contemplated by the prior art for use in cell culture applications have not been demonstrated to sustain cell growth for a number of passages. Those of skill in the art are aware that several passages are required to remove all traces of serum derived transferrin from a cell culture medium.

Culture Media Compositions

Any cell culture media may be prepared by the methods of the present invention. Particularly preferred media that may be prepared according to the invention include any cell culture media that supports the growth of animal cells, plant cells, bacterial cells, yeast cells or any type of cell known to those of skill in the art or disclosed herein. Generally, any media available or known in the art may be modified in accordance with the present invention (i.e., by addition of the metal binding compounds and/or transition metal complexes thereof). In a preferred aspect of the present invention, the metal binding compounds and/or transition element complexes thereof replace biologically derived (e.g. animal derived) transition element carriers such as serum, transferrin ceruloplasmin and the like.

Examples of animal cell culture media that may be prepared according to the present invention include, but are not limited to, DMEM, RPMI-1640, MCDB 131, MCDB 153, MDEM, IMDM, MEM, M199, McCoy's 5A, Williams' Media E, Leibovitz's L-15 Medium, Grace's Insect Medium, IPL-41 Insect Medium, TC-100 Insect Medium, Schneider's Drosophila Medium, Wolf & Quimby's Amphibian Culture Medium, cell-specific serum-free media (SFM) such as those designed to support the culture of keratinocytes, endothelial cells, hepatocytes, melanocytes, etc., F10 Nutrient Mixture and F12 Nutrient Mixture. Other media suitable for preparation by the invention are available commercially (e.g., from Life Technologies, Inc.; Rockville, Md. and Sigma; St. Louis, Mo.). Formulations for these media are well-known in the art and may be found, for example in the GIBCO/BRL Catalogue and Reference Guide (Life Technologies, Inc.; Rockville, Md.) and in the Sigma Animal Cell Catalogue (Sigma; St. Louis, Mo.).

Examples of plant cell culture media that may be prepared according to the present invention include, but are not limited to, Anderson's Plant Culture Media, CLC Basal Media, Gamborg's Media, Guillard's Marine Plant Culture Media, Provasoli's Marine Media, Kao and Michayluk's Media, Murashige and Skoog Media, McCown's Woody Plant Media, Knudson Orchid Media, Lindemann Orchid Media, and Vacin and Went Media. Formulations for these media, which are commercially available, as well as for many other commonly used plant cell culture media, are well-known in the art and may be found for example in the Sigma Plant Cell Culture Catalogue (Sigma; St. Louis, Mo.).

Examples of bacterial cell culture media that may be prepared according to the present invention include, but are not limited to, Trypticase Soy Media, Brain Heart Infusion Media, Yeast Extract Media, Peptone-Yeast Extract Media, Beef Infusion Media, Thioglycollate Media, Indole-Nitrate Media, MR-VP Media, Simmons' Citrate Media, CTA Media, Bile Esculin Media, Bordet-Gengou Media, Charcoal Yeast Extract (CYE) Media, Mannitol-salt Media, MacConkey's Media, Eosin-methylene blue (EMB) media, Thayer-Martin Media, Salmonella-Shigella Media, and Urease Media. Formulations for these media, which are commercially available, as well as for many other commonly used bacterial cell culture media, are well-known in the art and may be found for example in the DIFCO Manual (DIFCO; Norwood, Mass.) and in the Manual of Clinical Microbiology (American Society for Microbiology, Washington, D.C.).

Examples of fungal cell culture media, particularly yeast cell culture media, that may be prepared according to the present invention include, but are not limited to, Sabouraud Media and Yeast Morphology Media (YMA). Formulations for these media, which are commercially available, as well as for many other commonly used yeast cell culture media, are well-known in the art and may be found for example in the DIFCO Manual (DIFCO; Norwood, Mass.) and in the Manual of Clinical Microbiology (American Society for Microbiology, Washington, D.C.).

As the skilled artisan will appreciate, any of the above media of the invention may also include one or more additional components, such as indicating or selection agents (e.g., dyes, antibiotics, amino acids,. enzymes, substrates and the like), filters (e.g., charcoal), salts, polysaccharides, ions, detergents, stabilizers, and the like.

Metal Binding Compounds

The metal binding compounds of the present invention may be included in a medium formulation in an un-complexed form, i.e. not bound to a transition element. Alternatively, transition element complexes suitable for inclusion in media may be formed prior to inclusion in a medium formulation by combining one or more transition elements or ions thereof with one or more metal-binding compounds. When complexed prior to addition to a media formulation, the metal binding compounds of the present invention are preferably complexed to one or more transition elements. Preferred transition elements include, salts, or ions of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), rubidium (Ru), rhodium (Rh), palladium (Pd), silver (Ag), cadmium (Cd), lanthanum (La), hafnium (Hf), tantalum (Ta), tungsten (W), rhenium (Re), osmium (Os), iridium (Ir), platinum (Pt), gold (Au), mercury (Hg), and actinium (Ac). Particularly preferred transition elements for use in the complexes, compositions and media of the invention are iron (particularly ferrous ($Fe^{++}$) or ferric ($Fe^{+++}$) cations), zinc (particularly $Zn^{++}$), copper (particularly $Cu^{++}$, and manganese (particularly $Mn^{++}$). Such transition elements, metals, salts, and ions thereof are available commercially, for example from Sigma Aldrich Chemical Co. (St. Louis, Mo.).

Metal-binding compounds which may be advantageously used in preparing the transition element complexes and compositions of the invention include, but are not limited to, polyols (such as sorbitol and dextran), hydroxypyridine derivatives (including 2-hydroxypyridine-N-oxide, 3-hydroxy-4-pyrone, 3-hydroxypypyrid-2-one, 3-hydroxypyrid-2-one, 3-hydroxypyrid-4-one, 1-hydroxypyrid-2-one, 1,2-dimethyl-3-hydroxypyrid-4-one, 1-methyl-3-hydroxypyrid-2-one, 3-hydroxy-2(IH)-pyridinone, nicotinic acid-N-oxide, 2-hydroxy-nicotinic acid, pyridoxal isonicotinyl hydrazone, and the like; see U.S. Pat. Nos. 4,665,064, 4,861,767, 4,908,371, 5,256,676, 5,624,901, and 5,688,815),; LICAMS (1,5,10-N,N',N"-tris (5-sulfo-2,3-dihydroxybenzoyl)aminomethylbenzene), MECAM (1,3,5-N,N',N"-tris(2,3-dihydroxybenzoyl) aminomethylbenzene), EDTP (ethylenediamine-N,N'-tetramethylenephosphonic acid), trisuccin, acidic saccharides (e.g. ferrous gluconate) and glycosaminoglycans (see U.S. Pat. No. 5,707,604), DTPA (diethylenetriaminepentaacetic acid; see U.S. Pat. No. 5,746,995), acyl hydroxamate derivatives (e.g. acetohydroxarnic acid) (see U.S. Pat. Nos. 5,430,058, 5,506,266, and 5,756,825), amino acid derivatives (see U.S. Pat. Nos. 5,061,815, 5,278,329, and 5,430,164), deferoxamine, ferrioxamine, iron basic porphine and derivatives thereof, DOTA-lysine, texaphyrins, sapphyrins, polyaminocarboxylic acids (see U.S. Pat. Nos. 5,057,302, 5,227,474, 5,419,894 and 5,494,935), α-hydroxycarboxylic acids (see U.S. Pat. No. 5,583,243), polyethylenecarbamates (see U.S. Pat. No. 5,424,057), maltol, ethyl maltol, Ustilago ferrichrome, IRC011 (see Rivkin et al., *Blood* 90:4180–4187 (1997)), or combinations, derivatives, and complexes thereof. Particularly preferred for use in formulating the transition element complexes of the present invention are polyols (particularly sorbitol) and hydroxypyridine derivatives (particularly 2-hydroxypyridine-N-oxide). As described in detail in the Examples below, these compounds, particularly sorbitol and 2-hydroxypyridine-N-oxide, have been used successfully to replace transferrin as iron-carrying compounds in culture media useful for cultivation of mammalian cells. The metal-binding compounds used in accordance with the present invention may be obtained commercially (e.g., from Sigma, St. Louis, Mo. and other well-known commercial sources), or may be prepared synthetically according to the guidance provided by the technical and patent publications referenced herein, the disclosures of which are incorporated herein by reference in their entireties.

According to one aspect of the invention, the metal binding compounds of the present invention are added to a medium formulation. In preferred embodiments, the metal binding compounds of the present invention will be added to a medium formulation at a working concentration of from about 1 μM to about 500 μM which will be suitable for most cell types. According to another aspect of the invention, transition element complexes are prepared by admixing one or more transition elements, salts, or ions, preferably iron (especially in the form of $Fe^{++}$ or $Fe^{+++}$ cations or salts), with one or more metal-binding compounds, preferably one or more polyols (especially sorbitol) or one or more hydroxypyridine derivatives (especially 2-hydroxypyridine-N-oxide). These components are preferably admixed at a molar ratio of 1:1 to 1:6 (Iron carrier:$Fe^{++}$ or $Fe^{+++}$) although other suitable molar ratios may be readily determined by those of ordinary skill in the art. Once the transition element complexes of the invention have been formed, they may be added directly to any media to form the media of the invention. The complexes may be added to a final concentration suitable for the cultivation of the cells of interest. In preferred embodiments, a working concentration of from about 1 $\mu$M to about 500 $\mu$M will be used which is suitable for most cell types. The determination of the optimum concentration for a given cell line without undue experimentation is within the capability of one of ordinary skill in the art of cell culture. Alternatively, the complexes which are to be supplemented into a medium may be advantageously stored at 2–8° C. for at least 12 months prior to the addition to a medium.

The medium formulations of the present invention include one or more metal binding compounds and/or one or more metal binding compound in complex with a transition element. These complete media are suitable for use in the culture of a variety of animal cells, as described in more detail below. It may be preferable, however, to further enrich the nutritional content of the a given media to support faster growth and enhanced production of biologicals by the cultured cells, and to provide a more suitable environment for the culture of fastidious animal cells. To accomplish such enrichment, one or more additional nutrients derived from non-animal sources, such as extracts or enzymatic digests (including, e.g., peptones) of yeast or bacterial cells, plant peptides or lipids, and the like, may be added to the media of the invention.

The medium ingredients can be dissolved in a liquid carrier or maintained in dry form. If dissolved in a liquid carrier at the preferred concentrations shown in Table 1 (i.e., a "1×formulation"), the pH of the medium should be adjusted to about 6.8–7.5, preferably about 7.1–7.4, and, most preferably about 7.2–7.4. The osmolarity of the medium should also be adjusted to about 260–450 mOsm, preferably about 260–280 mOsm, and most preferably about 265–275 mOsm. The type of liquid carrier and the method used to dissolve the ingredients into solution vary and can be determined by one of ordinary skill in the art with no more than routine experimentation. Typically, the medium ingredients can be added in any order.

In one aspect of the invention, the culture media or solutions or compositions used to formulate the culture media may be formulated at 1×concentration. Alternatively, the solutions comprising ingredients and the culture media of the invention may be more concentrated than the concentration of the same ingredients in a 1×media formulation. For example, the media or ingredients can be 10-fold more concentrated (10×formulation), 20-fold more concentrated (20×formulation), 25-fold more concentrated (25× formulation), 50-fold more concentrated (50× concentration), 100-fold more concentrated (100× formulation), 500-fold more concentrated (500× formulation), or 1000-fold more concentrated (1000× formulation). More highly concentrated formulations can be made, provided that the ingredients remain soluble and stable. See U.S. Pat. No. 5,474,931, which is directed to methods of solubilizing culture media components at high concentrations.

If the media ingredients are prepared as separate concentrated solutions, an appropriate (sufficient) amount of each concentrate is combined with a diluent to produce a 1×medium formulation. Typically, the diluent used is water but other solutions including aqueous buffers, aqueous saline solution, or other aqueous solutions may be used according to the invention.

The culture media of the present invention are typically sterilized to prevent unwanted contamination. Sterilization may be accomplished, for example, by filtration through a low protein-binding membrane filter of about 0.1–0.45 $\mu$m pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1×sterile medium formulation. Autoclaving or other elevated temperature-based methods of sterilization are not favored, since a number of (he components of the present culture media may be heat labile. As will be readily apparent to one of ordinary skill in the art, the concentration of a given ingredient can be increased or decreased beyond the range disclosed and the effect of the increased or decreased concentration can be determined using only routine experimentation.

The optimization of the present media formulations was carried out using approaches described by Ham (Ham, R. G., *Methods for Preparation of Media, Supplements and Substrata for Serum-Free Animal Culture,* Alan R. Liss, Inc., New York, pp. 3–21 (1984)) and Waymouth (Waymouth, C., *Methods for Preparation of Media, Supplements and Substrata for Serum-Free Animal Culture,* Alan R. Liss, Inc., New York, pp. 23–68 (1984)). The optimal final concentrations for medium ingredients are typically identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth or continued health of the animal cells is measured.

As will be readily apparent to one of ordinary skill in the art, each of the components of the culture medium may react with one or more other components in the solution. Thus, the present invention encompasses the initial formulation as well as any reaction mixture, which forms after these ingredients are combined.

The present invention also relates to methods for replacing or substituting animal-derived products, particularly animal-derived transition element carriers with non-animal derived transition element carriers or complexes. Typical blood-derived products that may be replaced in accordance with this aspect of the invention include but are not limited to serum (e.g., fetal bovine serum and calf serum, human serum, etc.), plasma, transferrin, ceruloplasmin, albumin (e.g., bovine serum albumin or human serum albumin), antibodies, fibrinogen, factor VIII, etc. Other animal-derived medium components which may be replaced by one or more complexes in accordance with the invention can be easily determined by one of ordinary skill in the art by substituting one or more transition element carriers, preferably complexed with one or more transition elements (particularly iron, zinc, and/or manganese), in place of one or more animal-derived transition element carriers and testing the effect of such substitution on cell growth and cultivation by methods that will be familiar to the ordinarily skilled artisan (such as those methods described in the Examples below).

The present invention thus provides transition element carriers and/or complexes and compositions for use in cultivation of cells, particularly mammalian cells, in vitro. Such complexes and compositions may be used in a variety of medical (including diagnostic and therapeutic), industrial, forensic and research applications requiring ready-to-use serum-free media compositions for cultivation of a variety of cells.

The transition element carriers and/or complexes of the present invention may be used in conjunction with any media formulation known to those skilled in the art. In preferred embodiments, the transition metal complexes will be used with serum free media formulations.

Cell Sources

Cells which can be cultivated in media containing the non-protein metal binding compounds of the present invention may be eukaryotic or prokaryotic cells. In some preferred embodiments, cells which can be cultivated in the medium of the present invention are of eukaryotic origin, including but not limited to cells obtained from plants, mammals, birds (avian), insects, fish, amphibians, reptiles, and the like. Mammalian cells particularly suitable for cultivation in the present media include those of human origin, which may be primary cells derived from a tissue sample, diploid cell strains, transformed cells or established cell lines (e.g., HeLa), each of which may optionally be diseased or genetically altered. Other mammalian cells, such as hybridomas, CHO cells, COS cells, VERO cells, HeLa cells, 293 cells, PER-C6 cells, K562 cells, MOLT-4 cells, M1 cells, NS-1 cells, MDBK cells, MDCK cells, MRC-5 cells, WI-38 cells, WEHI cells, SP2/0 cells, BHK cells (including BHK-21 cells), primary and/or immortalized lymphocytes, macrophages, dendritic cells, keratinocytes, hepatocytes, neural cells, renal cells, fibroblasts, endothelial cells, tumor cells, epithelial cells, haematopoietic stem cells, mesenchymal stem cells, embryonic stem cells, stem cells of neuronal, hepatic, renal, dermal, endothelial, epithelial, and mesothelial origin, and derivatives thereof, are also suitable for cultivation in media containing the compounds of the present invention. In particular, stem cells and cells used in in vitro virus production may be cultivated in the media of the present invention. Insect cells particularly suitable for cultivation in the present media include those derived from Spodoptera species (e.g., Sf9 or Sf21, derived from *Spodoptera frugiperda*) or Trichoplusa species (e.g., HIGH FIVE™ or MG1, derived from *Trichoplusa ni*). Tissues, organs, organ systems and organisms derived from animals or constructed in vitro or in vivo using methods routine in the art may similarly be cultivated in the culture media of the present invention.

Culture of Cells

Cells can be plated according to the experimental conditions determined by the investigator. The example below demonstrates at least one functional set of culture conditions useful for cultivation of certain mammalian cells. It is to be understood, however, that the optimal plating and culture conditions for a given cell type can be determined by one of ordinary skill in the art using only routine experimentation. For routine culture conditions, using the present invention, cells can be plated onto the surface of culture vessels without attachment factors. Alternatively, the vessels can be pre-coated with natural, recombinant or synthetic attachment factors or peptide fragments (e.g., collagen or fibronectin, or natural or synthetic fragments thereof). Isolated cells can also be seeded into or onto a natural or synthetic three-dimensional support matrix such as a preformed collagen gel or a synthetic bio-polymeric material, or onto feeder layers of cells. Use of attachment factors or a support matrix with the medium of the present invention will enhance cultivation of many attachment-dependent cells in the absence of serum supplementation.

The cell seeding densities for each experimental condition can be optimized for the specific culture conditions being used. For routine culture in plastic culture vessels, an initial seeding density of $0.1$–$1.0 \times 10^5$ cells per $cm^2$ or about 1.5×the plating concentration routinely used for the same cells in serum supplemented media is preferable.

Mammalian cells are typically cultivated in a cell incubator at about 37° C., while the optimal temperatures for cultivation of avian, nematode and insect cells are typically somewhat lower and are well-known to those of ordinary skill in the art. The incubator atmosphere should be humidified for cultivation of animal cells, and should contain about 3–10% carbon dioxide in air. Culture medium pH should be in the range of about 7.1–7.6, preferably about 7.1–7.4, and most preferably about 7.1–7.3.

Cells in closed or batch culture should undergo complete medium exchange (i.e., replacing spent media with fresh media) about every 2–3 days, or more or less frequently as required by the specific cell type. Cells in perfusion culture (e.g., in bioreactors or fermentors) will receive fresh media on a continuously recirculating basis.

Cells may also be cultured in suspension in a shaker, stir-tank, air-lift, or perfusion culture. Some cell types (e.g. hybridoma, cells of lymphoid and myeloid origin) are inherently able to grow in suspension culture. Other cells (e.g. BHK, HeLa, 293, CHO) which may originally be cultivated in adherent culture may be induced to grow in suspension culture.

Cell Culture Composition

The cell culture media of the present invention may also be used to produce cell culture compositions comprising the present media and cells. The cells may be or eukaryotic or prokaryotic origin. Cells preferably used in such compositions include, but are not limited to, cells obtained from plants, mammals, birds (avian), insects or fish. Mammalian cells particularly suitable for use in such compositions include those of human origin, which may be primary cells derived from a tissue sample, diploid cell strains, transformed cells or established cell lines (e.g., HeLa), each of which may optionally be diseased or genetically altered. Other mammalian cells, such as hybridomas, CHO cells, COS cells, VERO cells, HeLa cells, 293 cells, PER-C6 cells, K562 cells, MOLT-4 cells, M1 cells, NS-1 cells, COS-7 cells, MDBK cells, MDCK cells, MRC-5 cells, WI-38 cells, SP2/0 cells, BHK cells (including BHK-21 cells), primary and/or immortalized lymphocytes, macrophages, dendritic cells, keratinocytes, hepatocytes, neural cells, renal cells, fibroblasts, endothelial cells, tumor cells, epithelial cells, haematopoietic stem cells, mesenchymal stem cells, embryonic stem cells, stem cells of neuronal, hepatic, renal, dermal, endothelial, epithelial, and mesothelial origin, and derivatives thereof, are also suitable for use in forming the cell culture compositions of the present invention. Insect cells particularly suitable for use in forming such compositions include those derived from Spodoptera species (e.g., Sf9 or Sf21, derived from *Spodoptera frugiperda*) or Trichoplusa species (e.g., HIGH FIVE™ or MG1, derived from *Trichoplusa ni*). Tissues, organs, organ systems and organisms derived from animals or constructed in vitro or in vivo using methods routine in the art may similarly be used to form the cell culture compositions of the present invention. These cell culture compositions may be used in a variety of medical (including diagnostic and therapeutic), industrial, forensic and research applications requiring ready-to-use cultures of cells in media.

Kits

The present invention also provides kits for use in cultivation of a variety of cells, including those cells described herein, for a number of medical (including diagnostic and therapeutic), industrial, forensic and research applications. Kits according to this aspect of the invention may comprise a carrier, such as a box, carton, tube or the like, having in close confinement therein one or more containers, such as vials, tubes, ampoules, bottles, pouches, envelopes, and the like. The kits of the invention may comprise one or more components selected from a group consisting of one or more media or media ingredients, one or more metal binding compounds, one or more transition element complexes comprising one or more metal binding compounds, one or more compositions of the invention and one or more cells and combinations thereof. According to this aspect of the invention, the one or more components may be contained within the same container, or may be in separate containers to be admixed prior to use in cultivation of cells. The kits may also comprise one or more additional components suitable for use in cultivation of cells, including, for example, one or more cytokines, one or more extracellular matrix components, one or more antibodies, one or more hormones (peptide or steroid), one or more enzymes, one or more growth supplements, one or more buffers or buffer salts, and the like. The kits of the present invention may also comprise one or more instructions or protocols for carrying out the methods of the present invention.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Semi-confluent adherent cultures of 293 Cells (ATCC, CRL 1573) are readily adapted to suspension culture. The cells are first detached with a solution of Trypsin-EDTA (0.05% Trypsin, 0.53 mM $Na_4$EDTA), and then resuspended in conventional medium supplemented with 10% FBS to inhibit the trypsin. The resuspended cells are centrifuged at 200×g for five minutes. The cell pellet is resuspended in 293 SFM (available from Life Technologies, Rockville, Md.) the formulation of which is described in WO 98/08934 which is specifically incorporated herein by reference. Alternatively, the cells may be detached with Versene ($Na_4$EDTA, 0.53 mM) and resuspended in 293 SFM.

The initial seeding density of the 293 cells after conversion to suspension culture is $1\times10^6$ cells/mL. The cells are shaken on a rotary shaker at 150 rpm in a 37° C. incubator equilibrated with 8% $CO_2$–92% air. When the cells reach a density of $1.5\times10^6$ cells/mL they are diluted with 293 SFM to a density of $3.0\times10^5$ cells/mL. Because 293 cells have a tendency to aggregate, the cells may be vortexed vigorously for approximately 45 seconds to obtain a predominantly single cell suspension at the time of passaging and counting. After several passages in suspension culture, the maximum achievable density may be determined. The 293 cells which are described here can grow to approximately $3-4\times10^6$ cells/mL in suspension culture.

The ability of metal binding compounds to support cellular growth was evaluated using 293 cells maintained in 293 SFM (Life Technologies, Rockville, Md.) without transferrin or metal binding compound. Stock cultures containing 5 µg/mL human holo-transferrin were prepared in 293 SFM. For metal binding compound evaluation, 293 cells were established in 125 mL shaker flasks at an initial viable seeding density of $2\times10^5$ cells/mL in a final volume of 20 mL. All cultures were maintained at 37° C. in humidified air containing 8% $CO_2$. To eliminate transferrin carry-over effects, cells were subcultured at 4 day intervals for a total of three passages. At each subculturing, cells were seeded at a density of $2\times10^5$ cells/mL. Positive control cultures contained 5 µg/mL human holo-transferrin while negative control cultures were established in the absence of either transferrin or metal binding compound. Metal binding compound stocks were prepared at 0.1M–0.2M in dd$H_2$O and solubilized when necessary using 5N NaOH or HCl. Iron complexes were established using 0.2M metal binding compound and iron stocks mixed 1:1 (v/v) and incubated for 5–10 minutes at 22° C. All solutions containing metal binding compounds were filter sterilized using a 0.22 µm Millex-GV filter prior to addition to transferrin and serum-free media.

In most cases, metal binding compounds were evaluated either alone or in combination with ferric chloride or ferrous sulfate at 25 µM, 50 µM and 100 µM. When used in combination, the metal binding compounds were used in equimolar concentration with iron ions. Values in the table represent the mean percentage of control growth for duplicate cultures determined at the third passage. Media that was not supplemented, i. e. did not contain either transferrin or metal binding compound, failed to support the growth of the cells over three passages.

The results of 293 cells grown in the presence of various metal binding compounds are shown in Table 1. When added to the medium formulation un-complexed, the metal binding compound is listed alone, when added as a complex with a transition metal, the source of the transition metal is listed with the metal binding compound.

TABLE 1

EFFECT OF METAL BINDING COMPOUNDS ON THE GROWTH OF 293 CELLS

| | Concentration | | |
|---|---|---|---|
| Metal binding compound tested | 25 µM | 50 µM | 100 µM |
| 2-Hydroxypyridine-N-Oxide (293 tested at 10–50 µM) | 117 | 150 | Not Tested |
| 3-Hydroxypyridine-N-Oxide | 4 | 4 | 4 |
| 3-Hydroxypyridine-N-Oxide · Ferric Chloride | 77 | 72 | 81 |
| 3-Hydroxypyridine-N-Oxide · Ferrous Sulfate | 104 | 58 | 0 |
| Sorbitol · Ferrous Sulfate | 58 | 69 | 83 |
| Deferoxamine Mesylate · Ferric Chloride | 101 (5 µM) | 120 (10 µM) | 127 (20 µM) |
| Acetohydroxamic Acid · Ferric Chloride | 83 | 22 | 0 |
| Serine Hydroxamate · Ferric Chloride | 68 | 65 | 51 |
| Glycine · Ferric Chloride | 81 | 71 | 72 |
| Nitriloacetic Acid · Ferric Chloride | 100 | 118 | 74 |

TABLE 1-continued

EFFECT OF METAL BINDING COMPOUNDS ON THE GROWTH OF 293 CELLS

| | Concentration | | |
|---|---|---|---|
| Metal binding compound tested | 25 μM | 50 μM | 100 μM |
| Nitriloacetic Acid · Ferrous Sulfate | 75 | 95 | 0 |
| 3-Hydroxy-2-Methyl-4-Pyrone (Maltol) | 0 | 28 | 81 |
| 2-Ethyl-3-Hydroxy-4-Pyrone (Ethyl Maltol) | 59 | 120 | 126 |
| 2,2-Dipyridylamine · Ferric Chloride | 118 | 96 | 101 |
| 2,2-Dipyridyl · Ferric Chloride | 51 | 96 | 0 |
| Diethylenetriamine Penta-Acetic Acid · Ferric Chloride | 79 | 96 | 102 |
| Diethylenetriamine Penta-Acetic Acid · Ferrous Sulfate | 77 | 107 | 85 |
| Nicotinic Acid-N-Oxide · Ferric Chloride | 104 | 80 | 79 |
| 2-Hydroxynicotinic Acid · Ferric Chloride (293 tested at 100, 150, 200 μM) | 0 | 0 | 99 |
| Ferrous Gluconate · Ascorbic Acid Phosphate | 86 | 109 | 101 |
| Aspartic Acid · Ferric Chloride | 81 | 86 | 100 |
| Glutamic Acid · Ferric Chloride | 102 | 68 | 83 |
| N-Acetyl-Cysteine · Ferric Chloride | 88 | 82 | 52 |
| 4-Pyridoxic Acid · Ferric Chloride | 109 | 85 | 99 |
| 2-Pyridinecarboxylic Acid · Ferrous Sulfate | 67 | 48 | 0 |
| Myo-Inositol · Ferric Chloride | 79 | 87 | 85 |
| Mimosine · Ferric Chloride | 64 | 55 | 80 |
| Ferrous Sulfate | 71 | 60 | 41 |
| Ferric Chloride | 87 | 91 | 109 |

EXAMPLE 2

The ability of metal binding compounds to support cellular growth in the absence of transferrin was evaluated using CHO cells maintained in CD CHO medium (Life Technologies, Rockville, Md., the formulation of which is described in WO 98/08934). Stock cultures containing 5 μg/mL human holo-transferrin were prepared in CD CHO medium. For metal binding compound evaluation, CHO cells were established in 125 mL shaker flasks at an initial viable seeding density of $1 \times 10^5$ cells/mL in a final volume of 20 mL. All cultures were maintained at 37° C. in humidified air containing 8% $CO_2$. To eliminate transferrin carry-over effects, cells were subcultured at 4 day intervals for a total of three passages. Positive control cultures contained 5 μg/mL human holo-transferrin while negative control cultures were established in the absence of either transferrin or metal binding compound. Metal binding compound stocks were prepared at 0.1M–0.2M in $ddH_2O$ and solubilized when necessary using 5N NaOH or HCl. Iron complexes were established using 0.2M metal binding compound and iron stocks mixed 1:1 (v/v) and incubated for 5–10 minutes at 22° C. All solutions containing metal binding compounds were filter sterilized using a 0.22 μm Millex-GV filter prior to addition to transferrin and serum-free media.

In most cases, metal binding compounds were evaluated either alone or in combination with ferric chloride or ferrous sulfate at 25 μM, 50 μM and 100 μM. Values in the table represent the mean percentage of control growth for duplicate cultures determined at the third passage. Media that was not supplemented, i. e. did not contain either transferrin or metal binding compounds, failed to support the growth of the cells over three passages.

The ability of various metal binding compounds to substitute for transferrin in the culture of CHO cells was determined. The results are shown in Table 2. When added to the medium formulation un-complexed, the metal binding compound is listed alone, when added as a complex with a transition metal, the source of the transition metal is listed with the metal binding compound.

TABLE 2

EFFECT OF METAL BINDING COMPOUNDS ON THE GROWTH OF CHO CELLS

| | Conc. | | |
|---|---|---|---|
| Metal binding compound tested | 25 μM | 50 μM | 100 μM |
| 2-Hydroxypyridine-N-Oxide | 127 | 117 | 83 |
| 3-Hydroxypyridine-N-Oxide · Ferric Chloride | 77 | 66 | 101 |
| Sorbitol · Ferric Chloride | 100 | 107 | 112 |
| Deferoxamine Mesylate · Ferric Chloride | 50 | 74 | 52 |
| | (5 μM) | (10 μM) | (20 μM) |
| Serine Hydroxamate · Ferric Chloride | 106 | 121 | 124 |
| Lysine · Ferric Chloride | 51 | 79 | 98 |
| Nitriloacetic Acid · Ferric Chloride | 127 | 107 | 107 |
| 2-Ethyl-3-Hydroxy-4-Pyrone | 9 | 60 | 113 |
| 2,2-Dipyridylamine · Ferric Chloride | 40 | 48 | 65 |
| Diethylenetriamine Penta-Acetic Acid · Ferrous Sulfate | 135 | 137 | 147 |
| Nicotinic Acid-N-Oxide · Ferric Chloride | 60 | 84 | 105 |
| Ferrous Gluconate · Ascorbic Acid Phosphate | 91 | 61 | 28 |
| Aspartic Acid · Ferric Chloride | 77 | 89 | 112 |
| Cysteine · Ferrous Sulfate | 83 | 64 | 45 |
| 4-Pyridoxic Acid · Ferric Chloride | 55 | 63 | 100 |
| 2-Pyridinecarboxylic Acid · Ferric Chloride | 88 | 89 | 100 |
| Kojic Acid | 0 | 0 | 0 |
| Kojic Acid · Ferric Chloride | 89 | 88 | 85 |
| 2,3-Dihydrobenzoic Acid · Ferric Chloride | 71 | 0 | 0 |
| Ferrous Sulfate | 88 | 79 | 38 |
| Ferric Chloride | 56 | 85 | 101 |

EXAMPLE 3

The ability of iron metal binding compounds to support cellular growth in the absence of transferrin was evaluated using Sp2/0 cells maintained in CD Hybridoma medium (Life Technologies, Rockville, Md.). Stock cultures containing 5 μg/mL human holo-transferrin were prepared in CD Hybridoma medium. For metal binding compound evaluation, Sp2/0 cells were established at an initial viable cell density of $0.5 \times 10^5$ cells/mL in stationary culture using 75 $cm^2$ tissue culture flasks in a final volume of 20 mL. All cultures were maintained at 37° C. in humidified air containing 8% $CO_2$. To eliminate transferrin carry-over effects, cells were subcultured at the same seeding density at 4 day intervals for a total of three passages. Positive control cultures contained 5 μg/mL human holotransferrin while negative control cultures were established in the absence of either transferrin or metal binding compound. Metal binding compound stocks were prepared at 0.1M–0.2M in $ddH_2O$ and solubilized when necessary using 5N NaOH or HCl. Iron complexes were established using 0.2M metal binding compound and iron stocks mixed 1:1 (v/v) and incubated for 5–10 minutes at 22° C. All solutions containing metal binding compounds were filter sterilized using a 0.22 μm Millex-GV filter prior to addition to transferrin and serum-free media.

In most cases, metal binding compounds were evaluated either alone or in combination with ferric chloride or ferrous sulfate at 25 μM, 50 μM and 100 μM. Values in the table represent the mean percentage of control growth for duplicate cultures determined at the third passage. Media that was not supplemented, i. e. did not contain either transferrin or metal binding compounds, failed to support the growth of the cells over three passages.

The ability of various metal binding compounds to substitute for transferrin in the culture of Sp2/0 cells was determined and the results are seen in Table 3. When added to the medium formulation un-complexed, the metal binding compound is listed alone, when added as a complex with a transition metal, the source of the transition metal is listed with the metal binding compound.

TABLE 3

EFFECT OF METAL BINDING COMPOUNDS ON THE GROWTH OF Sp2/0 CELLS

| Metal binding compound tested | Conc. | | |
|---|---|---|---|
| | 25 μM | 50 μM | 100 μM |
| 2-Hydroxypyridine-N-Oxide | 98 | 93 | 89 |
| 3-Hydroxypyridine-N-Oxide · Ferric Chloride | 55 | 54 | 57 |
| Sorbitol · Ferric Chloride | 94 | 55 | 60 |
| Deferoxamine Mesylate · Ferric Chloride | 0 | 0 | 0 |
| (All lines tested at 5, 10, 20 μM) | (5 μM) | (10 μM) | (20 μM) |
| Acetohydroxamic Acid · Ferric Chloride | 40 | 48 | 47 |
| (Sp2 tested at 5, 10, 20 μM) | | | |
| Serine Hydroxamate · Ferric Chloride | 46 | 66 | 62 |
| Glycine · Ferric Chloride | 34 | 61 | 56 |
| Nitriloacetic Acid · Ferric Chloride | 88 | 87 | 70 |
| Nitriloacetic Acid | 0 | 0 | 0 |
| 3-Hydroxy-2-Methyl-4-Pyrone (Maltol) | 0 | 0 | 0 |
| 3-Hydroxy-2-Methyl-4-Pyrone · Ferric Chloride | 60 | 71 | 75 |
| 2-Ethyl-3-Hydroxy-4-Pyrone (Ethyl Maltol) | 0 | 75 | 116 |
| Diethylenetriamine Penta-Acetic Acid · Ferrous Sulfate | 54 | 90 | 91 |
| 2-Hydroxynicotinic Acid · Ferric Chloride | 64 | 82 | 85 |
| Ferrous Gluconate · Ascorbic Acid Phosphate | 92 | 94 | 93 |
| Glutamine · Ferric Chloride | 36 | 55 | 65 |
| Asparagine · Ferric Chloride | 36 | 51 | 54 |
| Cysteine · Ferrous Sulfate | 85? | 79 | 67 |
| 4-Pyridoxic Acid · Ferric Chloride | 40 | 73 | 76 |
| 2-Pyridinecarboxylic Acid · Ferric Chloride | 0 | 30 | 48 |
| Morpholine · Ferric Chloride | 54 | 64 | 81 |
| 3-Hydroxy-2-Nitropyridine · Ferric Chloride | 52 | 62 | 72 |
| Kojic Acid | 0 | 0 | 0 |
| Kojic Acid · Ferric Chloride | 0 | 0 | 0 |
| Ferrous Sulfate | 91 | 103 | 94 |
| Ferric Chloride | 55 | 73 | 74 |

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A serum free mammalian cell culture medium comprising at least one transition metal binding compound or at least one transition element complex, said complex comprising at least one transition element or a salt or ion thereof complexed to at least one transition metal-binding compound, wherein said medium is capable of supporting the cultivation of a mammalian cell in vitro, wherein said transition metal-binding compound is a hydroxypyridine derivative selected from the group consisting of 2-hydroxypyridine-N-oxide, 3-hydroxy-4-pyrone, 3-hydroxypypyrid-2-one, 1-methyl-3-hydroxypyrid-2-one, and 2-hydroxy-nicotinic acid.

2. The medium of claim 1, wherein said transition element is selected from the group consisting of scandium, titanium, vanadium, chromium, manganese, iron, cobalt, nickel, copper, zinc, yttrium, zirconium, niobium, molybdenum, technetium, rubidium, rhodium, palladium, silver, cadmium, lanthanum, hafnium, tantalum, tungsten, rhenium, osmium, iridium, platinum, gold, mercury, actinium, and salts thereof.

3. The medium of claim 1, wherein said transition element is iron, or a salt or ion of iron.

4. The medium of claim 1, wherein said hydroxypyridine derivative is 2-hydroxypyridine-N-oxide.

5. The medium of claim 1, wherein said transition element ion is a ferrous ion or a ferric ion.

6. The medium of claim 3, wherein said salt of said transition element salt is $FeCl_3$.

7. The cell culture medium of claim 1, said medium further comprising one or more ingredients selected from the group of ingredients consisting of at least one amino acid, at least one vitamin, at least one inorganic salt, at least one organic salt, at least one trace metal, at least one nucleotide, at least one buffering salt, at least one sugar, at least one lipid and at least one hormone.

8. The cell culture medium of claim 1, wherein said cells are selected from a group consisting of 293 cells, PER-C6 cells, CHO cells, COS cells and Sp2/0 cells.

9. The cell culture medium of claim 1, wherein said medium is a defined medium.

10. The medium of claim 9, wherein said transition element is iron, or a salt or ion thereof.

11. The medium of claim 1, wherein said medium does not contain transferrin.

12. The medium of claim 1, wherein said medium does not contain animal derived metal carriers.

13. The medium of claim 1, wherein said medium is a 1×medium formulation.

14. The medium of claim 1, wherein said medium is a concentrated medium formulation.

15. A serum-free mammaliam cell culture medium obtained by combining a cell culture medium with at least one transition metal binding compound or at least one transition element complex, said complex comprising at least one transition element or a salt or ion thereof complexed to at least one transition metal-binding compound, wherein said medium is capable of supporting the cultivation of a mammaliam cell in vitro, wherein said metal-binding compound is a hydroxypyridine derivative selected from the group consisting of 2-hydroxypyridine-N-oxide, 3-hydroxy-4-pyrone, 3-hydroxypyrid-2-one, 1-hydroxypyrid-2-one 1-methyl-3-hydroxypyrid-2-one, and 2-hydroxy-nicotinic acid.

16. The medium obtained according to claim 15, wherein said hydroxypyridine derivative is 2-hydroxypyridine-N-oxide.

17. The medium obtained according to claim 15, wherein said transition element ion is a ferrous ion or a ferric ion.

18. The medium obtained according to claim 17, wherein said salt of said transition element salt is $FeCl_3$.

19. A kit for the cultivation of a cell in vitro, said kit comprising:
(a) at least one first container containing at least one first component selected from the group consisting of one or more mammalian cell culture media or media ingredients, and one or more cells, and
(b) at least one second container containing at least one second component selected from the group consisting of one or more transition metal binding compounds and at least one transition element complex, said complex comprising at least one transition element or a salt or ion thereof complexed to at least one transition metal-binding compound wherein said transition metal-binding compound is a hydroxypyridine derivative selected from the group consisting of 2-hydroxypyridine-N-oxide, 3-hydroxy-4-pyrone, 3-hydroxypyrid-2-one, 1-hydroxypyrid-2-one, 1-methyl-3-hydroxypyrid-2-one and 2-hydroxynicotinic acid.

20. The kit of claim 19, wherein said transition element is selected from the group consisting of scandium, titanium, van adium, chromium, manganese, iron, cobalt, nickel, copper, zinc, yttrium, zirconium, niobium, molybdenum, technetium, rubidium, rhodium, palladium, silver, cadmium, lanthanum, hafnium, tantalum, tungsten, rhenium, osmium, iridim, platinum, gold, mercury, actinium, and salts thereof.

21. The kit of claim 19, wherein said transition element is iron, or a salt or ion thereof.

* * * * *

UNITED STATES PATENT AND TRADEMARK OFFICE
CERTIFICATE OF CORRECTION

PATENT NO. : 6,767,741 B1
APPLICATION NO. : 09/650339
DATED : July 27, 2004
INVENTOR(S) : David A. Epstein et al.

It is certified that error appears in the above-identified patent and that said Letters Patent is hereby corrected as shown below:

Col. 24 line 7
Claim 1, line 11, "3-hydroxypypyrid-2-one" should read --3-hydroxypyrid-2-one, 1-hydroxypyrid-2-one--.

Claim 6, line 1, "3" should read --1--.

Claim 13, line 2, "1xmedium" should read --1X medium--.

Claim 15, line 12, "1-hydroxypyrid-2-one 1-methyl-3-hydroxypyrid-2-one," should read --1-hydroxypyrid-2-one, 1-methyl-3-hydroxypyrid-2-one,--.

Claim 20, line 3, "van adium" should read --vanadium--.

Signed and Sealed this

Third Day of April, 2007

JON W. DUDAS
*Director of the United States Patent and Trademark Office*